(12) United States Patent
Wong

(10) Patent No.: US 9,148,912 B2
(45) Date of Patent: Sep. 29, 2015

(54) DISINFECTING AND TIDYING DEVICE FOR QUILT

(71) Applicant: Kwok Wai Wong, Shenzhen (CN)

(72) Inventor: Kwok Wai Wong, Shenzhen (CN)

(73) Assignee: Guangpei Min, Shen zhen (CN)

( * ) Notice: Subject to any disclaimer, the term of this patent is extended or adjusted under 35 U.S.C. 154(b) by 58 days.

(21) Appl. No.: 14/184,717

(22) Filed: Feb. 20, 2014

(65) Prior Publication Data

US 2015/0237678 A1    Aug. 20, 2015

(51) Int. Cl.
| | |
|---|---|
| A61L 2/00 | (2006.01) |
| A61L 9/00 | (2006.01) |
| G01N 23/00 | (2006.01) |
| A61N 5/00 | (2006.01) |
| F26B 3/34 | (2006.01) |
| F26B 13/10 | (2006.01) |
| H05B 1/02 | (2006.01) |
| A61L 2/20 | (2006.01) |
| A61L 2/10 | (2006.01) |

(52) U.S. Cl.
CPC ............... *H05B 1/0272* (2013.01); *A61L 2/10* (2013.01); *A61L 2/202* (2013.01)

(58) Field of Classification Search
CPC ............. A61L 2/00; A61L 2/22; A61L 2/202; A47K 17/00; F26B 13/00
USPC .................. 422/1, 24, 28, 292, 305, 307; 250/455.11, 492.1; 34/275, 523
See application file for complete search history.

(56) References Cited

U.S. PATENT DOCUMENTS

2011/0044848 A1* 2/2011 Wright .............................. 422/24

* cited by examiner

*Primary Examiner* — Monzer R Chorbaji
(74) *Attorney, Agent, or Firm* — Min-Lee Teng; Litron Patent & Trademark Office

(57) ABSTRACT

A disinfecting and tidying device for a quilt includes a heating housing and a disinfecting unit. The heating housing includes a top cover and a bottom cover. The top cover and the bottom cover respectively include a frame and heating members configured in the frame. Portions of the frames of the top cover and the bottom cover adjacent to the open are curved. The disinfecting unit is located in the heating housing. The disinfecting unit and the heating housing together define a disinfecting room for accommodating the quit. The disinfecting unit is a hollow structure and includes an upper plate, a lower plate and a plurality of disinfecting members. Ends of the upper plate and the lower plate adjacent to the open are connected with each other in a curved manner. The disinfecting and tidying device can be used to disinfect, dry and tidy the quilt easily and conveniently.

7 Claims, 3 Drawing Sheets

DISINFECTING AND TIDYING DEVICE FOR QUILT

BACKGROUND

1. Technical Field

The present invention relates to a device used for bedclothes in daily life, and more particularly to a disinfecting and tidying device for a quilt.

2. Description of the Related Art

Usually, human life has a third of the time spent in sleep. Sleep quality and sleep environment are very important for people. Naturally, beds, bedclothes and others supplied for sleep may influence sleep quality and sleep environment. Metabolism and perspiration will occur in sleep of human. The perspiration may wet the bedclothes. Specially, in some air moist areas, the bedclothes are easier to be moist. Warm and moist bedclothes are easy to breed bacteria. Therefore, if the bedclothes are neglected to clean and disinfect for a long time, the people's health would be affected.

In addition, health of the bedclothes in public health environment is also an important problem, such as hotels, hospitals and other public services. In order to prevent cross-infection and spread of bacteria, the bedclothes should be disinfected timely.

BRIEF SUMMARY

The present invention relates to a new disinfecting and tidying device for a quilt that can be used to disinfect, dry and tidy the quilt easily and conveniently.

To achieve at least one of the above-mentioned advantages, the present invention provides a disinfecting and tidying device for a quilt. The disinfecting and tidying device for a quilt includes a heating housing and a disinfecting unit. The heating housing includes a top cover and a bottom cover. The top cover and the bottom cover respectively have a first end and a second end on opposite sides thereof. The first ends of the top cover and the bottom cover are rotatably connected with each other. The second ends of the top cover and the bottom cover define an open. The top cover and the bottom cover respectively include a frame and heating members configured in the frame. Portions of the frames of the top cover and the bottom cover adjacent to the open are curved. The disinfecting unit is located in the heating housing. The disinfecting unit and the heating housing together define a disinfecting room for accommodating the quit. The disinfecting unit is a hollow structure and includes an upper plate, a lower plate and a plurality of disinfecting members. Ends of the upper plate and the lower plate adjacent to the open are connected with each other in a curved manner.

In an embodiment of the present invention, the disinfecting members are configured on the upper plate and the lower plate respectively.

In an embodiment of the present invention, the disinfecting members are configured in a room that defined between the upper plate and the lower plate.

In an embodiment of the present invention, the disinfecting member includes a UV generator.

In an embodiment of the present invention, the disinfecting unit includes an ozone generator.

In an embodiment of the present invention, the heating member has a heating wire therein.

In an embodiment of the present invention, the disinfecting and tidying device further includes a controller connected to the heating members and the disinfecting members correspondingly.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Reference will now be made to the drawings to describe various exemplary embodiments of the present disinfecting and tidying device for the quilt in detail.

Figure 1:
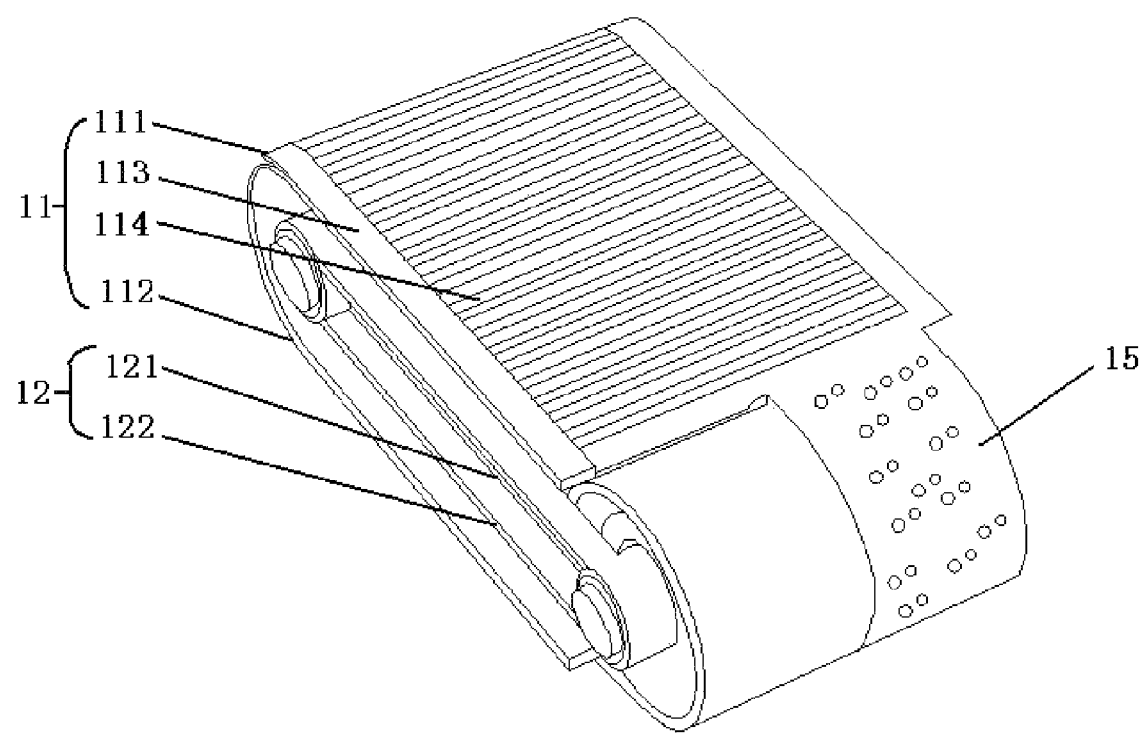
FIG. 1 is a schematic view of a disinfecting and tidying device for a quilt according to an exemplary embodiment of the present invention.
Figure 2:
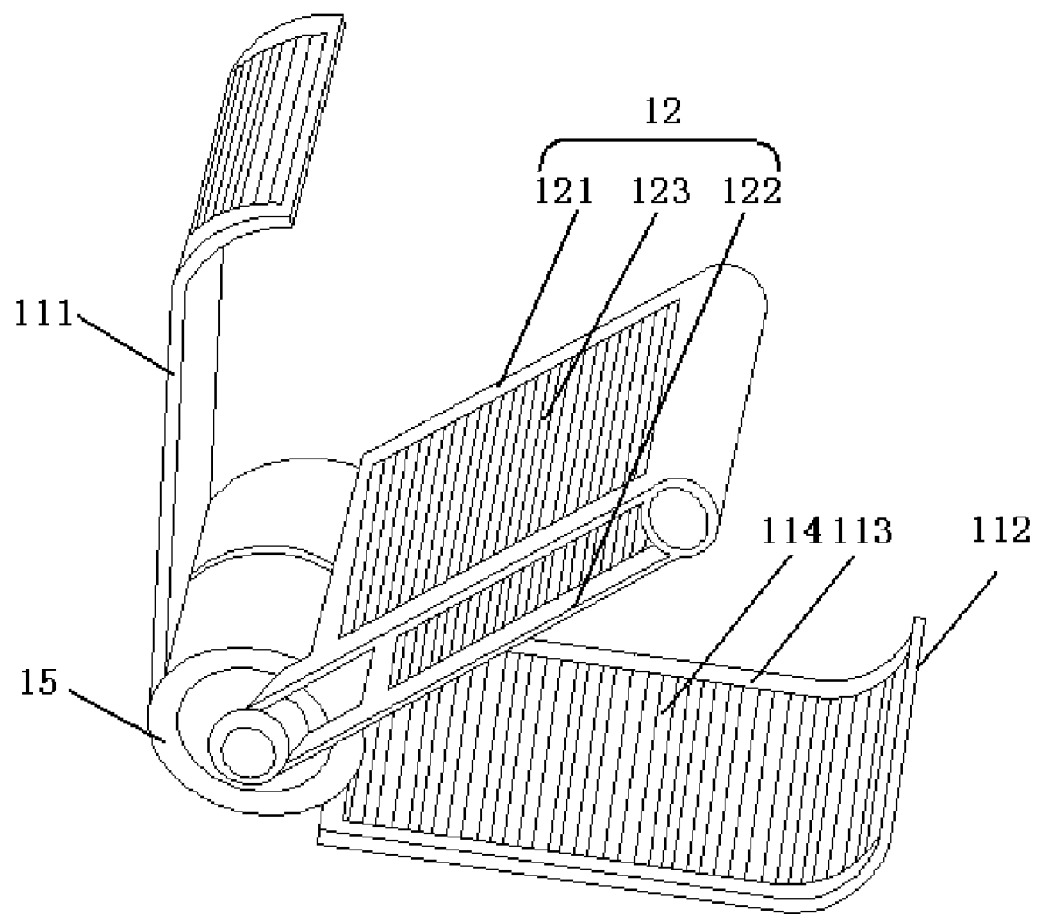
FIG. 2 shows the disinfecting and tidying device for the quilt of FIG. 1 being opened.
Figure 3:
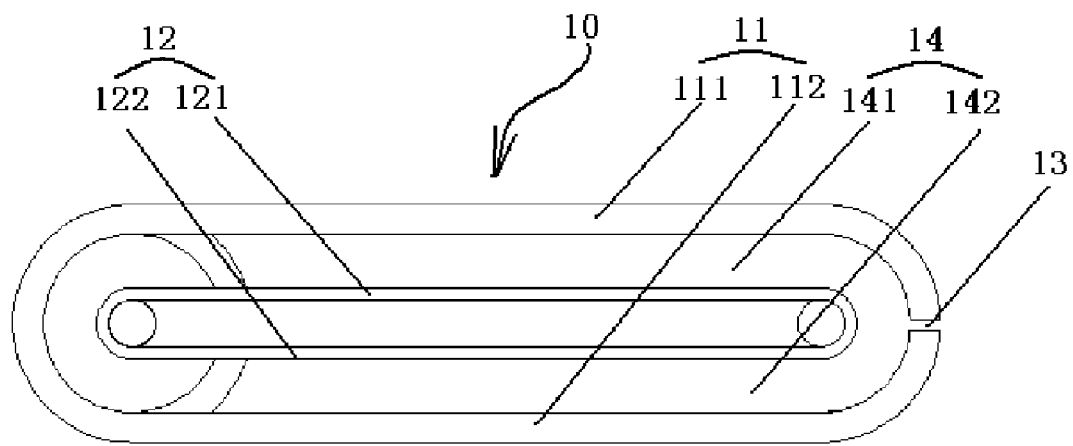
FIG. 3 is a side view of the disinfecting and tidying device for the quilt of FIG. 1

Referring to FIGS. 1 to 3, a disinfecting and tidying device 10 that can be used for a quit is shown. The disinfecting and tidying device 10 includes a heating housing 11 and a disinfecting unit 12. The heating housing 11 includes a top cover 111 and a bottom cover 112. The top cover 111 has a first end and a second end on opposite sides of the top cover 111. The bottom cover 112 also has a first end and a second end on opposite sides of the bottom cover 112. The first ends of the top cover 111 and the bottom cover 112 are rotatably connected with each other. The second ends of the top cover 111 and the bottom cover 112 define an open 13. The open 13 can be opened and closed by rotating the top cover 111 and the bottom cover 112 correspondingly. The top cover 111 includes a frame 113 and heating members 114. The bottom cover 112 also includes a frame 113 and heating members 114. The heating members 114 are configured in the frame 113. Portions of the frames 113 of the top cover 111 and the bottom cover 112 are adjacent to the open 13 being curved, so that the frames 113 can be suitable to tidy the quit.

The disinfecting unit 12 is located in the heating housing 11. The disinfecting unit 12 and the heating housing 11 together define a disinfecting room 14 for accommodating the quit. The disinfecting unit 12 is a hollow structure and includes an upper plate 121 and a lower plate 122. A plurality of disinfecting members 123 are configured on the upper plate 121 and the lower plate 122 respectively. Ends of the upper plate 121 and the lower plate 122 that are adjacent to the open 13 are connected with each other in a curved manner, so that the disinfecting unit 12 can be suitable to tidy the quit. It should be understood that, the disinfecting members 123 can be configured in a room that defined between the upper plate 121 and the lower plate 122.

The heating members 114 can includes a heating wire therein. The heating wire is used to generate heat to dry the quit, so that the quit can be dried.

The disinfecting member 123 can includes a UV generator therein. The UV generator can be used to generate UV light to disinfect the quit. In another exemplary embodiment, the disinfecting member 123 can includes an ozone generator therein. The ozone generator can be used to generate ozone to disinfect the quit.

The disinfecting room 14 can be divided into an upper disinfecting room 141 and a lower disinfecting room 142. The upper disinfecting room 141 is located between the top cover 111 and the upper plate 121 of the disinfecting unit 12. The lower disinfecting room 142 is located between the bottom cover 112 and the lower plate 122 of the disinfecting unit 12. In use, when the open 13 is opened by rotating the top cover 111 and the bottom cover 112 correspondingly, the quit can be tidied into the disinfecting room 14. Then the open 13 is closed by rotating the top cover 111 and the bottom cover 112, and the quit can be dried and disinfected in the disinfecting and tidying device 10. In the disinfecting room 14, a portion of the quit can be in the upper disinfecting room 141, and another portion of the quit can be in the lower disinfecting room 142.

Furthermore, the disinfecting and tidying device 10 can include a controller 15. The controller 15 can be connected to the heating members 114 and the disinfecting members 123 correspondingly. By the controller 15, if the quit is tidied in the disinfecting and tidying device 10, the quit could be controlled to be dried and/or disinfected automatically, so that the use of the disinfecting and tidying device 10 can be more convenient.

The above disinfecting and tidying device 10 includes the heating housing 11 and the disinfecting unit 12. The heating housing 11 can be used to dry the quit, and the disinfecting unit 12 can be used to disinfect the quit. As such, the quit can be disinfected, dried and tidied easily and conveniently. As such, while the quit is used, cross-infection and spread of bacteria can be prevented. Therefore, the health of the bedclothes can be easily obtained by the disinfecting and tidying device 10.

The above description is given by way of example, and not limitation. Given the above disclosure, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A disinfecting and tidying device for a quilt comprising:
   a heating housing comprising a top cover and a bottom cover, the top cover and the bottom cover respectively having a first end and a second end on opposite sides thereof, the first ends of the top cover and the bottom cover rotatably connected with each other, the second ends of the top cover and the bottom cover defining an open, the top cover and the bottom cover respectively comprising a frame and heating members configured in the frame, portions of the frames of the top cover and the bottom cover adjacent to the open being curved; and
   a disinfecting unit located in the heating housing, the disinfecting unit and the heating housing together defining a disinfecting room for accommodating the quilt, the disinfecting unit being a hollow structure and comprising an upper plate, a lower plate and a plurality of disinfecting members, ends of the upper plate and the lower plate adjacent to the open being connected with each other in a curved manner.

2. The disinfecting and tidying device for a quilt as claimed in claim 1, wherein the disinfecting members are configured on the upper plate and the lower plate respectively.

3. The disinfecting and tidying device for a quilt as claimed in claim 1, wherein the disinfecting members are configured in a room that defined between the upper plate and the lower plate.

4. The disinfecting and tidying device for a quilt as claimed in claim 1, wherein the disinfecting member comprises a UV generator.

5. The disinfecting and tidying device for a quilt as claimed in claim 1, wherein the disinfecting unit comprises an ozone generator.

6. The disinfecting and tidying device for a quilt as claimed in claim 1, wherein the heating member has a heating wire therein.

7. The disinfecting and tidying device for a quilt as claimed in claim 1, wherein the disinfecting and tidying device further comprises a controller connected to the heating members and the disinfecting members correspondingly.

* * * * *